(12) United States Patent
Horiuchi et al.

(10) Patent No.: US 11,079,503 B2
(45) Date of Patent: Aug. 3, 2021

(54) RADIATION DETECTION DEVICE

(71) Applicant: FUJIFILM Corporation, Tokyo (JP)

(72) Inventors: Hisatsugu Horiuchi, Kanagawa (JP); Masateru Tateishi, Kanagawa (JP); Shinsuke Noguchi, Kanagawa (JP)

(73) Assignee: FUJIJFILM Corporation, Tokyo (JP)

( * ) Notice: Subject to any disclaimer, the term of this patent is extended or adjusted under 35 U.S.C. 154(b) by 259 days.

(21) Appl. No.: 16/228,068

(22) Filed: Dec. 20, 2018

(65) Prior Publication Data

US 2019/0196033 A1  Jun. 27, 2019

(30) Foreign Application Priority Data

Dec. 22, 2017 (JP) .............................. JP2017-246655

(51) Int. Cl.
*G01T 7/00* (2006.01)
*G01T 1/20* (2006.01)
(Continued)

(52) U.S. Cl.
CPC .............. *G01T 7/00* (2013.01); *A61B 6/4283* (2013.01); *A61B 6/4411* (2013.01);
(Continued)

(58) Field of Classification Search
CPC ..... G01T 1/2018; G01T 1/20188; G01T 1/24; G01T 1/244; A61B 6/4411; A61B 6/4283
See application file for complete search history.

(56) References Cited

U.S. PATENT DOCUMENTS

2007/0272873 A1\* 11/2007 Jadrich ................. G01T 1/2018
250/370.11
2012/0069966 A1 3/2012 Kobayashi
(Continued)

FOREIGN PATENT DOCUMENTS

JP 2011-141154 A 7/2011
JP 2012-063326 A 3/2012
(Continued)

OTHER PUBLICATIONS

Japanese Office Action, dated Jan. 5, 2021, for corresponding Japanese Application No. 2017-246655, with an English machine translation.

*Primary Examiner* — Michael C Bryant
(74) *Attorney, Agent, or Firm* — Birch, Stewart, Kolasch & Birch, LLP.

(57) ABSTRACT

A radiation detection device includes: a radiation detection panel; a supporting member having a first surface and a second surface being opposite to the first surface, wherein the radiation detection panel is provided at a side of the first surface; first and second power supply units that supply operating electric power of the radiation detection panel; a housing that accommodates the radiation detection panel, the supporting member, and the first power supply unit; and a holder portion which is provided on the second surface of the supporting member and to which the second power supply unit is detachably attached, the holder portion includes a pair of frames that protrude toward a bottom of the housing which faces the second surface of the supporting member and a concave portion as defined herein, and the bottom of the housing has an opening portion through which the concave portion is exposed.

19 Claims, 3 Drawing Sheets

(51) Int. Cl.
  *G01T 1/24* (2006.01)
  *A61B 6/00* (2006.01)

(52) U.S. Cl.
  CPC ........ *G01T 1/2018* (2013.01); *G01T 1/20188* (2020.05); *G01T 1/24* (2013.01); *G01T 1/244* (2013.01)

(56) References Cited

U.S. PATENT DOCUMENTS

| | | | | |
|---|---|---|---|---|
| 2012/0076266 | A1* | 3/2012 | Kim | A61B 6/56 378/62 |
| 2013/0075619 | A1 | 3/2013 | Sugizaki et al. | |
| 2014/0211921 | A1* | 7/2014 | Bandis | H01M 2/08 378/91 |
| 2014/0226795 | A1* | 8/2014 | Kitano | A61B 6/4283 378/189 |
| 2014/0232841 | A1* | 8/2014 | Ohta | H05G 1/60 348/65 |
| 2014/0252229 | A1 | 9/2014 | Kondo | |
| 2015/0293237 | A1 | 10/2015 | Suzuki et al. | |
| 2016/0089092 | A1 | 3/2016 | Shimizukawa et al. | |
| 2016/0206276 | A1 | 7/2016 | Kobayashi | |
| 2016/0299237 | A1 | 10/2016 | Kondo | |
| 2017/0090044 | A1 | 3/2017 | Suzuki | |
| 2018/0368789 | A1 | 12/2018 | Shimizukawa et al. | |

FOREIGN PATENT DOCUMENTS

| | | |
|---|---|---|
| JP | 2013-72809 A | 4/2013 |
| JP | 2013-72810 A | 4/2013 |
| JP | 2014-173895 A | 9/2014 |
| JP | 2015-78920 A | 4/2015 |
| JP | 2015-200606 A | 11/2015 |
| JP | 2016-70758 A | 5/2016 |
| JP | 2017-67564 A | 4/2017 |
| JP | 2018-81030 A | 5/2018 |

* cited by examiner

RADIATION DETECTION DEVICE

CROSS-REFERENCE TO RELATED APPLICATIONS

This application claims the benefit of Japanese Patent Application JP 2017-246655, filed Dec. 22, 2017, the entire content of which is hereby incorporated by reference, the same as if set forth at length.

BACKGROUND OF THE INVENTION

1. Field of the Invention

The present invention relates to a radiation detection device.

2. Description of the Related Art

A so-called flat panel detector (FPD) is used to acquire a radiographic image of an object. The FPD comprises, for example, a scintillator that emits fluorescence corresponding to the amount of incident radiation and a detection substrate on which pixels detecting the fluorescence emitted from the scintillator are two-dimensionally arranged. Radiation transmitted through the object is incident on the scintillator and each pixel converts the fluorescence generated from the scintillator into an electric signal. Radiographic image data of the object is generated on the basis of the electric signal output from each pixel. In addition, a so-called electronic cassette which is portable and in which an FPD is accommodated in a housing has been known as a radiation detection device comprising an FPD.

The electronic cassette comprises a battery that supplies power to the FPD. For example, in a radiographic image detection device disclosed in JP2011-141154A, a battery is accommodated in a housing that accommodates an FPD. In a radiographic image detection device disclosed in JP2013-072809A, a battery is fitted to a battery accommodation portion provided in a housing that accommodates an FPD. A radiography apparatus disclosed in JP2014-173895A and a radiography apparatus disclosed in JP2015-200606A have been known as an electronic cassette to which an external battery is attached as the radiographic image detection device disclosed in JP2013-072809A.

SUMMARY OF THE INVENTION

In the electronic cassette provided with a battery as the radiographic image detection device disclosed in JP2011-141154A, the battery is protected by the housing. Therefore, it is possible to omit the housing only for the battery or to reduce the thickness of the housing. This configuration is advantageous in reducing the weight of the electronic cassette. However, in a case in which the battery is gone, it takes a lot of time to charge the battery and it is difficult to respond to a request for emergency use.

In the electronic cassette to which an external battery is attached as the radiographic image detection device disclosed in JP2013-072809A, in a case in which the battery is gone, the battery is replaced with another battery and it is possible to flexibly respond to a request for emergency use. However, the housing only for the battery needs to be relatively strongly configured, which is disadvantageous in reducing the weight of the electronic cassette.

For example, the electronic cassette is inserted between the bed and an object that lies on his or her side on the bed and is then used. The load of the object is applied to the electronic cassette. In the radiographic image detection device disclosed in JP2013-072809A, in a state in which the battery is detached from the battery accommodation portion of the housing, there is a space in the battery accommodation portion of the housing to which the battery is fitted and the rigidity of the housing is reduced. In a case in which a load is applied to the radiographic image detection device in this state, the housing and the FPD accommodated in the housing are deformed due to a reduction in the rigidity of the housing. As a result, there is a concern that the FPD will be damaged.

The invention has been made in view of the above-mentioned problems and an object of the invention is to provide a radiation detection device that can prevent the damage of a radiation detection panel, reduce the weight of the radiation detection panel, and respond to a request for emergency use.

According to an aspect of the invention, there is provided a radiation detection device comprising: a radiation detection panel; a supporting member having a first surface on which the radiation detection panel is provided; first and second power supply units that supply operating power of the radiation detection panel; a housing that accommodates the radiation detection panel, the supporting member, and the first power supply unit; and a holder portion which is provided on a second surface opposite to the first surface of the supporting member and to which the second power supply unit is detachably attached. The holder portion includes a pair of frames that protrude toward a bottom of the housing which faces the second surface of the supporting member and a concave portion that is formed between the pair of frames and is capable of accommodating the second power supply unit. The bottom of the housing has an opening portion through which the concave portion is exposed.

According to the invention, it is possible to provide a radiation detection device that can prevent the damage of a radiation detection panel, reduce the weight of the radiation detection panel, and respond to a request for emergency use.

DESCRIPTION OF THE PREFERRED EMBODIMENTS

Figure 1:
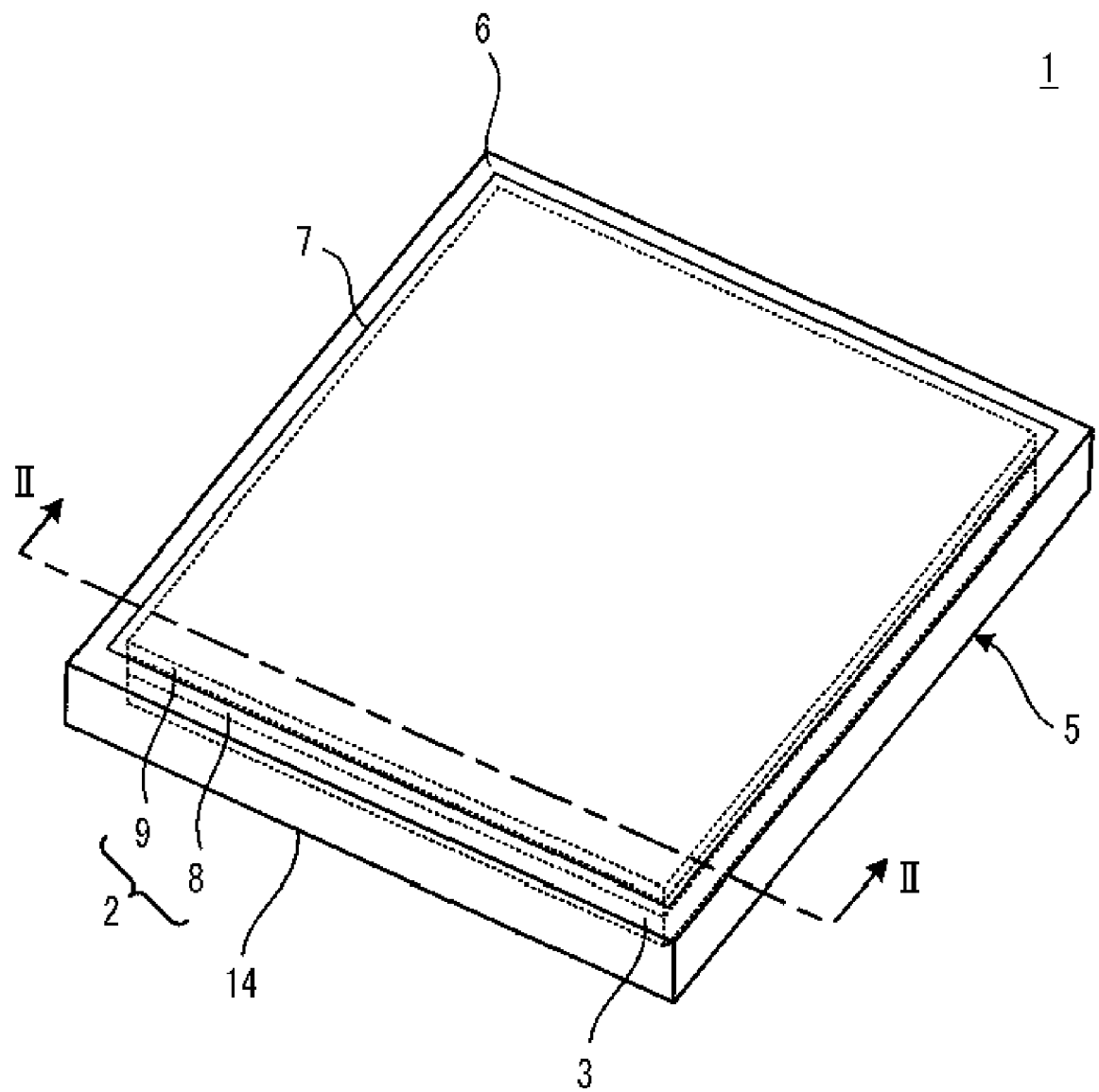
FIG. 1 is a perspective view illustrating an example of a radiation detection device for describing an embodiment of the invention.
Figure 2:
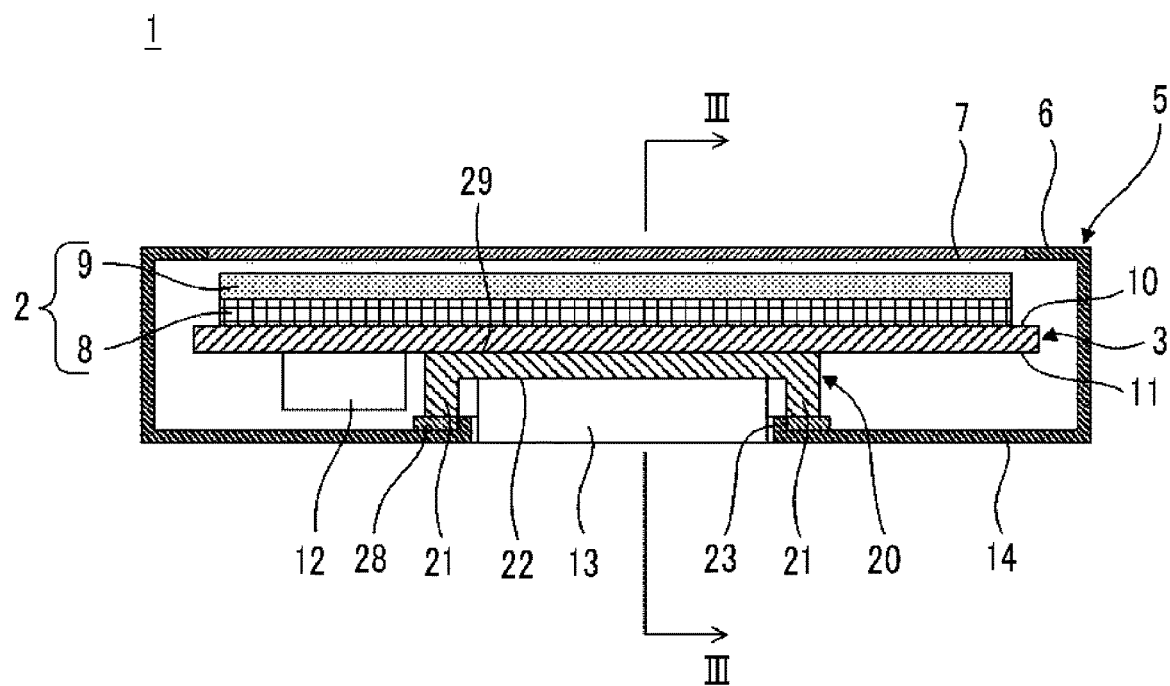
FIG. 2 is a cross-sectional view illustrating the radiation detection device taken along the line II-II of FIG. 1.
Figure 3:
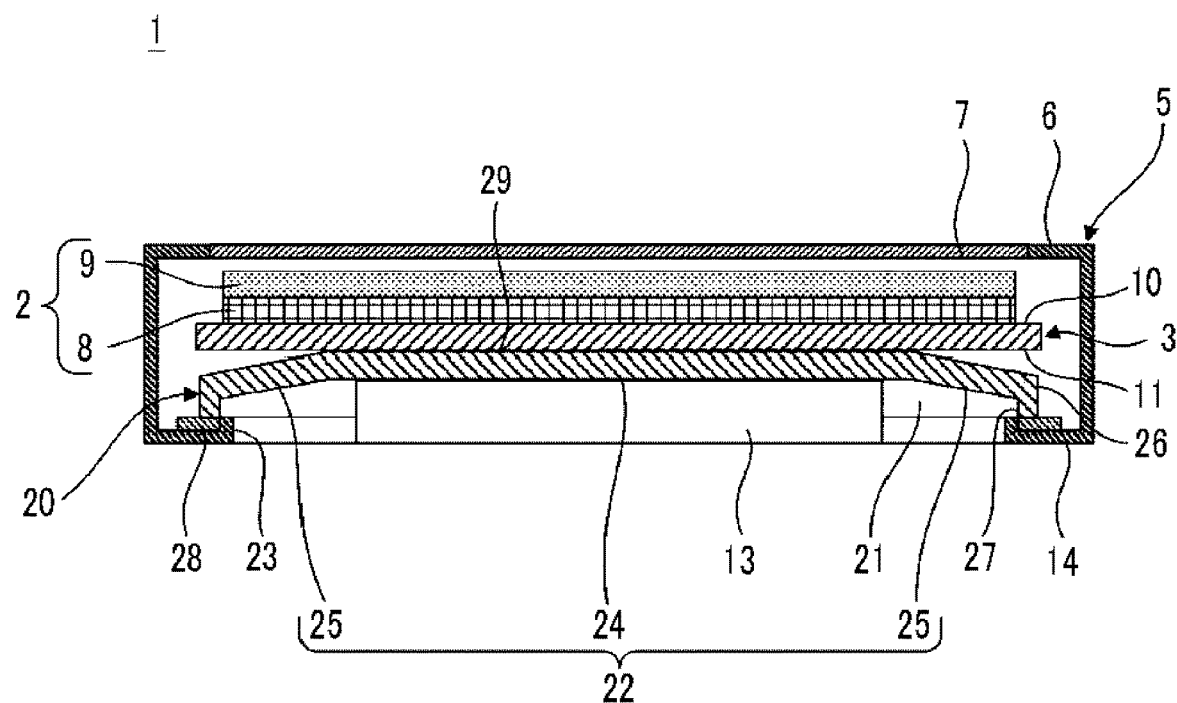
FIG. 3 is a cross-sectional view illustrating the radiation detection device taken along the line III-III of FIG. 2.

FIGS. 1 to 3 illustrate an example of a radiation detection device for describing an embodiment of the invention.

A radiation detection device 1 illustrated in FIGS. 1 to 3 is a so-called electronic cassette and comprises a radiation detection panel 2 that detects radiation, such as X-rays, a supporting member 3, a housing 5 that accommodates the radiation detection panel 2 and the supporting member 3, and first and second power supply units 12 and 13 that supply power to the radiation detection panel 2.

The housing 5 is formed in a rectangular parallelepiped shape and typically has a size based on the International Organization for Standardization (ISO) 4090:2001. It is preferable that the housing 5 is made of a material which can reduce weight and increase load resistance. Examples of the material include a magnesium alloy, an aluminum alloy, a fiber reinforced resin, a cellulose nanofiber (CNF) reinforced resin, and a resin that satisfy a specific gravity of 3.0 or less and a Young's modulus of 1.8 GPa or more. A rectangular opening is formed in a top plate 6 of the housing 5. A transmission plate 7 that transmits radiation is attached to the opening.

The radiation detection panel 2 includes a scintillator 8 and a detection substrate 9 and is provided behind the transmission plate 7 in the housing 5. The scintillator 8 has a phosphor, such as CsI:Tl (thallium-activated cesium iodide) or GOS ($Gd_2O_2S$:Tb, terbium-activated gadolinium oxysulfide), and emits fluorescence corresponding to the amount of incident radiation. The detection substrate 9 includes a plurality of pixels that are two-dimensionally arranged, detects fluorescence generated by the scintillator 8 with the pixels, and converts the detected fluorescence into an electric signal.

In this example, the scintillator 8 and the detection substrate 9 are stacked in the order of the scintillator 8 and the detection substrate 9 from the transmission plate 7 of the housing 5. However, the scintillator 8 and the detection substrate 9 may be stacked in the order of the detection substrate 9 and the scintillator 8 from the transmission plate 7. In addition, a direct-conversion-type radiation detection panel may be used in which a photoconductive film of each pixel of the detection substrate 9 that generates signal charge is made of, for example, amorphous selenium and which directly converts radiation into signal charge.

The supporting member 3 is a plate-shaped member and is formed in a rectangular shape. In the specification, the rectangular shape is not limited to a quadrangle with right-angled corners and includes a quadrangle with chamfered corners or a quadrangle with rounded corners. The supporting member 3 has a first surface 10 that faces the top plate 6 of the housing 5 and a second surface 11 that is opposite to the first surface 10. The radiation detection panel 2 is provided on the first surface 10 of the supporting member 3. In addition, the radiation detection panel 2 may be attached to the supporting member 3 or may be attached to the top plate 6 and the transmission plate 7 of the housing 5. It is preferable that the supporting member 3 is made of a material which can reduce weight and increase load resistance. Examples of the material include a magnesium alloy, an aluminum alloy, a fiber reinforced resin, a cellulose nanofiber (CNF) reinforced resin, and a resin that satisfy a specific gravity of 3.0 or less and a Young's modulus of 1.8 GPa or more.

The first power supply unit 12 and the second power supply unit 13 are rechargeable batteries, such as lithium-ion secondary batteries, or capacitors, such as electric double layer capacitors or lithium-ion capacitors. The first power supply unit 12 is bonded to the second surface 11 of the supporting member 3 and is accommodated in the housing 5. In addition, a circuit substrate is bonded to the second surface 11 of the supporting member 3, which is not illustrated in the drawings. For example, a driving control circuit that controls the driving of the detection substrate 9, a signal processing circuit that processes the electric signal output from the detection substrate 9, a communication circuit for communication with the outside, and a power circuit are formed on the circuit substrate.

A holder portion 20 to which the second power supply unit 13 is detachably attached is provided on the second surface 11 of the supporting member 3. The holder portion 20 includes a pair of frames 21 that protrude toward a bottom 14 of the housing 5 which faces the second surface 11 of the supporting member 3 and a concave portion 22 that is provided between the pair of frames 21. The concave portion 22 is formed so as to accommodate the second power supply unit 13. An opening portion 23 through which the concave portion 22 is exposed is formed in the bottom 14 of the housing 5. The second power supply unit 13 is accommodated into the concave portion 22 from the outside of the housing 5 through the opening portion 23. In a state in which the second power supply unit 13 is accommodated in the concave portion 22, the outer surface of the second power supply unit 13 exposed through the opening portion 23 is disposed so as to be flush with the outer surface of the bottom 14 of the housing 5 or is disposed inside the housing 5 so as to be lower than the outer surface of the bottom 14.

As illustrated in FIG. 3, the concave portion 22 includes an accommodation portion 24 that accommodates the second power supply unit 13 and a slope portion 25 that is adjacent to both sides of the accommodation portion 24 in a direction in which the pair of frames 21 extend. The slope portion 25 is inclined so as to become closer to the second surface 11 of the supporting member 3 as it becomes closer to the accommodation portion 24 in the direction in which the pair of frames 21 extend and functions as a guide in a case in which the second power supply unit 13 is inserted into the accommodation portion 24. This configuration makes it easy to attach the second power supply unit 13 to the holder portion 20. In this example, the slope portion 25 is provided so as to be adjacent to both sides of the accommodation portion 24 in the direction in which the pair of frames 21 extend. However, the slope portion 25 may be provided so as to be adjacent at least one of both sides in the direction in which the pair of frames 21 extend.

An end 26 of the slope portion 25 which is opposite to the accommodation portion 24 extends to an outer peripheral portion of the bottom 14 of the housing 5. A step portion 27 which can be grasped by the user of the radiation detection device 1 is provided between the end 26 of the slope portion 25 and the bottom 14 of the housing 5. The step portion 27 makes it possible to prevent the portable radiation detection device 1 from falling from the hand of the user in a case in which the user carries the radiation detection device 1 and to prevent the damage of the radiation detection panel 2 caused by an impact at the time of the falling. In addition, the sentence "the step portion 27 can be grasped" means that there is a level difference to the extent that a finger is hooked between the end 26 of the slope portion 25 and the bottom 14 of the housing 5 and that there is a level difference of, for example, 2 mm or more.

A sealing member 28 is interposed between the bottom 14 of the housing 5 and the holder portion 20 (the pair of frames 21 and the end 26 of each of the slope portions 25 provided on both sides) along the edge of the opening portion 23. The sealing member 28 is an elastic body, such as silicone rubber or a foamed body. The sealing member 28 prevents the infiltration of water into the housing 5 and the transmission of light into the housing 5.

One or both of the first power supply unit 12 and the second power supply unit 13 supply power to the radiation detection panel 2 and the circuit substrate in a state in which the second power supply unit 13 is attached to the holder portion 20. The first power supply unit 12 supplies power to the radiation detection panel 2 and the circuit substrate in a state in which the second power supply unit 13 is detached from the holder portion 20. That is, even in a case in which the second power supply unit 13 is detached from the holder portion 20, the radiation detection device 1 can be used by the first power supply unit 12. Therefore, in normal times, the radiation detection device 1 is used in a state in which the external second power supply unit 13 is detached. As a result, it is possible to reduce the weight of the radiation detection device 1. Even in a case in which the first power supply unit 12 is gone, the radiation detection device 1 can be used by attaching the second power supply unit 13 to the holder portion 20. In addition, the radiation detection device 1 can respond a request for emergency use.

The holder portion 20 provided on the second surface 11 of the supporting member 3 includes the pair of frames 21 that protrude toward the bottom 14 of the housing 5 and the bending rigidity of the supporting member 3 is increased by the pair of frames 21. In a case in which the second power supply unit 13 is detached from the holder portion 20, there is a space in the opening portion 23 of the housing 5 and the concave portion 22 of the holder portion 20 exposed through the opening portion 23. However, since the bending rigidity of the supporting member 3 is increased by the pair of frames 21, the supporting member 3 is prevented from sinking into the space in the opening portion 23 and the concave portion 22. Therefore, it is possible to prevent the damage of the radiation detection panel 2 supported by the supporting member 3.

Preferably, the pair of frames 21 extend along the long sides of the rectangular supporting member 3. The long side is more likely to warp than the short side in the rectangular supporting member 3. Since the pair of frames 21 extend along the long sides of the supporting member 3, it is possible to effectively prevent the warpage of the supporting member 3 and to further prevent the damage of the radiation detection panel 2.

The holder portion 20 may be formed integrally with the supporting member 3. In a case in which the supporting member 3 is made of a metal material, such as an aluminum alloy or a magnesium alloy, the holder portion 20 may be formed integrally with the supporting member 3 by, for example, casting or forging. In a case in which the supporting member 3 is made of a resin material, such as a fiber reinforced resin, the holder portion 20 may be formed integrally with the supporting member 3 by, vacuum molding. In addition, the holder portion 20 may be formed separately from the supporting member 3 and may be bonded to the second surface 11 of the supporting member 3. In the examples illustrated in FIGS. 2 and 3, the holder portion 20 is formed separately from the supporting member 3 and is then bonded to the second surface 11 of the supporting member 3. In this case, it is preferable that a bonding surface 29 of the holder portion 20 to the second surface 11 of the supporting member 3 is entirely bonded to the second surface 11 in order to increase the bending rigidity of the supporting member 3. In a case in which the holder portion 20 is formed separately from the supporting member 3, the material forming the holder portion 20 is not particularly limited. It is preferable that the holder portion 20 is made of a material which can reduce weight and increase load resistance. Examples of the material include a magnesium alloy, an aluminum alloy, a fiber reinforced resin, a cellulose nanofiber (CNF) reinforced resin, and a resin that satisfy a specific gravity of 3.0 or less and a Young's modulus of 1.8 GPa or more.

Figure 4:
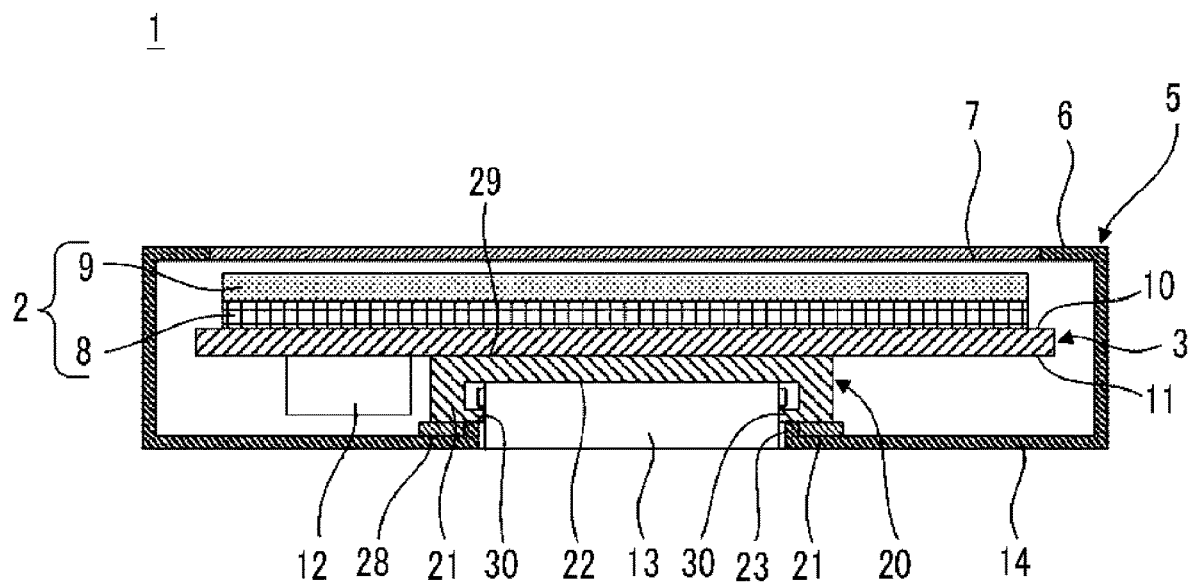
FIG. 4 is a cross-sectional view illustrating a modification example of the radiation detection device illustrated in FIG. 1.

As illustrated in FIG. 4, ribs 30 that protrude in a direction in which the pair of frames 21 face each other may be provided at leading ends of the pair of frames 21. The second moment of area of the pair of frames 21 is increased by the ribs 30. Therefore, it is possible to further increase the bending rigidity of the supporting member 3 and to further prevent the damage of the radiation detection panel 2. In addition, the second power supply unit 13 that is accommodated in the accommodation portion 24 formed between the pair of frames 21 can be locked by the ribs 30. Therefore, it is possible to prevent the second power supply unit 13 from falling off from the holder portion 20.

Figure 5:
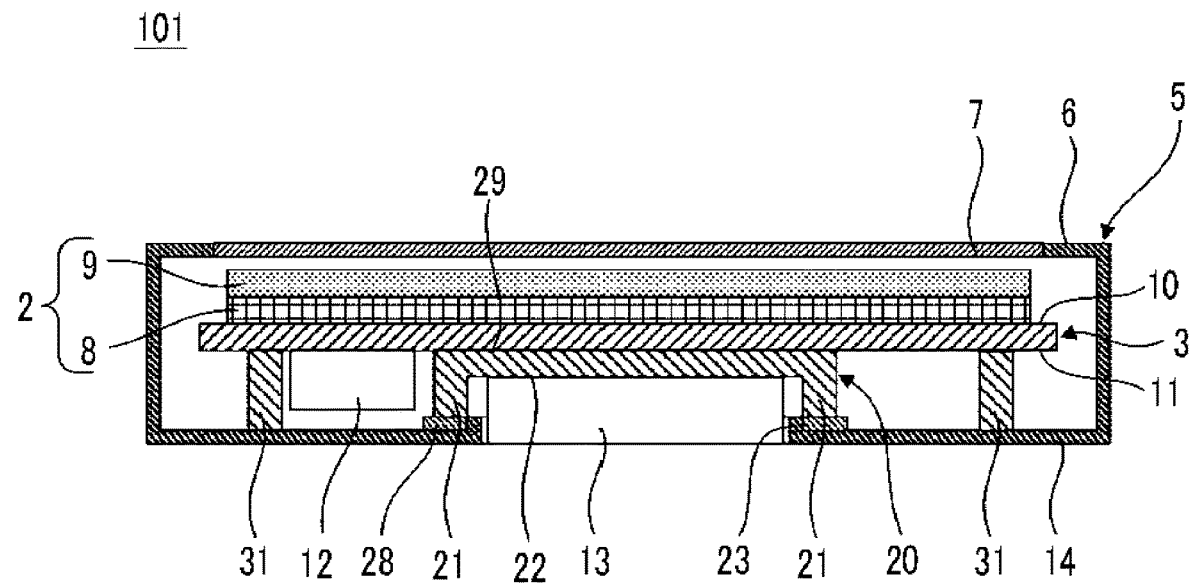
FIG. 5 is a cross-sectional view illustrating another example of the radiation detection device for describing the embodiment of the invention.

FIG. 5 illustrates another example of the radiation detection device for describing the embodiment of the invention. The same components as those in the above-mentioned radiation detection device 1 are denoted by the same reference numerals and the description thereof will not be repeated or the components will be described in brief.

A radiation detection device 101 illustrated in FIG. 5 differs from the radiation detection device 1 in that it further comprises a plurality of spacers 31. The plurality of spacers 31 are provided on the second surface 11 of the supporting member 3 separately from the holder portion 20. The plurality of spacers 31 protrude from the pair of frames 21 of the holder portion 20 to the bottom 14 of the housing 5 and come into contact with the bottom 14 of the housing 5. In a case in which, for example, the load of the object or an impact caused by falling is applied to the radiation detection device 101, the supporting member 3 is supported by the plurality of spacers 31. Therefore, the sealing member 28 interposed between the bottom 14 of the housing 5 and the holder portion 20 is prevented from being excessively compressed. As a result, it is possible to prevent the deterioration of the sealing member 28 and to more reliably prevent the infiltration of water into the housing 5 and the transmission of light into the housing 5.

As described above, a radiation detection device disclosed in the specification comprises: a radiation detection panel; a supporting member having a first surface on which the radiation detection panel is provided; first and second power supply units that supply operating power of the radiation detection panel; a housing that accommodates the radiation detection panel, the supporting member, and the first power supply unit; and a holder portion which is provided on a second surface opposite to the first surface of the supporting member and to which the second power supply unit is detachably attached. The holder portion includes a pair of frames that protrude toward a bottom of the housing which faces the second surface of the supporting member and a concave portion that is formed between the pair of frames and is capable of accommodating the second power supply unit. The bottom of the housing has an opening portion through which the concave portion is exposed.

The radiation detection device disclosed in the specification further comprises a sealing member that is interposed between the bottom of the housing and the holder portion along an edge of the opening portion.

The radiation detection device disclosed in the specification further comprises a plurality of spacers that are provided on the second surface of the supporting member separately from the holder portion and come into contact with the bottom of the housing.

In the radiation detection device disclosed in the specification, ribs that protrude in a direction in which the pair of frames face each other are provided at leading ends of the pair of frames.

In the radiation detection device disclosed in the specification, the concave portion includes an accommodation portion that accommodates the second power supply unit and a slope portion that is provided so as to be adjacent to at least one of both sides of the accommodation portion in a direction in which the pair of frames extend. The slope portion becomes closer to the second surface as becoming closer to the accommodation portion in the direction in which the pair of frames extend.

In the radiation detection device disclosed in the specification, the slope portion has a step portion that is provided between an end opposite to the accommodation portion and the bottom of the housing and is capable of being grasped.

In the radiation detection device disclosed in the specification, the holder portion is formed integrally with the supporting member.

In the radiation detection device disclosed in the specification, the holder portion is formed separately from the supporting member and is bonded to the second surface, and a bonding surface of the holder portion to the second surface is entirely bonded to the second surface.

EXPLANATION OF REFERENCES 1, 101: radiation detection device
2: radiation detection panel
3: supporting member
5: housing
6: top plate
7: transmission plate
8: scintillator
9: detection substrate
10: first surface of supporting member
11: second surface of supporting member
12: first power supply unit
13: second power supply unit
14: bottom of housing
20: holder portion
21: frame
22: concave portion
23: opening portion
24: accommodation portion
25: slope portion
26: end of slope portion
27: step portion
28: sealing member
29: bonding surface
30: rib
31: spacer

What is claimed is:

1. A radiation detection device comprising:
a radiation detection panel;
a supporting member having a first surface and a second surface being opposite to the first surface, wherein the radiation detection panel is provided at a side of the first surface;
first and second power supply units that supply operating electric power of the radiation detection panel;
a housing that accommodates the radiation detection panel, the supporting member, and the first power supply unit; and
a holder portion which is provided on the second surface of the supporting member and to which the second power supply unit is detachably attached,
wherein the holder portion comprises a pair of frames that protrude toward a bottom of the housing which faces the second surface of the supporting member and a concave portion that is provided between the pair of frames and is capable of accommodating the second power supply unit, and
the bottom of the housing has an opening portion through which the concave portion is exposed to an outside of the housing.

2. The radiation detection device according to claim 1, further comprising:
a sealing member that is interposed between the bottom of the housing and the holder portion along an edge of the opening portion.

3. The radiation detection device according to claim 1, further comprising:
a plurality of spacers that are provided on the second surface of the supporting member separately from the holder portion so that the plurality of spacers contact with the bottom of the housing.

4. The radiation detection device according to claim 2, further comprising:
a plurality of spacers that are provided on the second surface of the supporting member separately from the holder portion so that the plurality of spacers contact with the bottom of the housing.

5. The radiation detection device according to claim 1, wherein ribs that protrude in a direction in which the pair of frames face each other are provided at leading ends of the pair of frames.

6. The radiation detection device according to claim 2, wherein ribs that protrude in a direction in which the pair of frames face each other are provided at leading ends of the pair of frames.

7. The radiation detection device according to claim 3, wherein ribs that protrude in a direction in which the pair of frames face each other are provided at leading ends of the pair of frames.

8. The radiation detection device according to claim 1, wherein the concave portion comprises an accommodation portion that accommodates the second power supply unit and a slope portion that is provided so as to be adjacent to at least one of both sides of the accommodation portion in a direction in which the pair of frames extend, and
the slope portion becomes closer to the second surface as becoming closer to the accommodation portion in the direction in which the pair of frames extend.

9. The radiation detection device according to claim 2, wherein the concave portion comprises an accommodation portion that accommodates the second power supply unit and a slope portion that is provided so as to be adjacent to at least one of both sides of the accommodation portion in a direction in which the pair of frames extend, and
the slope portion becomes closer to the second surface as becoming closer to the accommodation portion in the direction in which the pair of frames extend.

10. The radiation detection device according to claim 3, wherein the concave portion comprises an accommodation portion that accommodates the second power supply unit and a slope portion that is provided so as to be adjacent to at least one of both sides of the accommodation portion in a direction in which the pair of frames extend, and
the slope portion becomes closer to the second surface as becoming closer to the accommodation portion in the direction in which the pair of frames extend.

11. The radiation detection device according to claim 8, wherein the slope portion has a step portion that is provided between an end opposite to the accommodation portion and the bottom of the housing and is capable of being grasped.

12. The radiation detection device according to claim 9, wherein the slope portion has a step portion that is provided between an end opposite to the accommodation portion and the bottom of the housing and is capable of being grasped.

13. The radiation detection device according to claim 10, wherein the slope portion has a step portion that is provided between an end opposite to the accommodation portion and the bottom of the housing and is capable of being grasped.

14. The radiation detection device according to claim 1, wherein the holder portion is formed integrally with the supporting member.

15. The radiation detection device according to claim 2, wherein the holder portion is formed integrally with the supporting member.

16. The radiation detection device according to claim 3, wherein the holder portion is formed integrally with the supporting member.

17. The radiation detection device according to claim 1, wherein the holder portion is formed separately from the supporting member and is bonded to the second surface, and a whole area of a surface of the holder portion which is bonded to the second surface is bonded to the second surface.

18. The radiation detection device according to claim 2, wherein the holder portion is formed separately from the supporting member and is bonded to the second surface, and a whole area of a surface of the holder portion which is bonded to the second surface is bonded to the second surface.

19. The radiation detection device according to claim 3, wherein the holder portion is formed separately from the supporting member and is bonded to the second surface, and a whole area of a surface of the holder portion which is bonded to the second surface is bonded to the second surface.

\* \* \* \* \*